US010113990B2

(12) United States Patent
Burge et al.

(10) Patent No.: US 10,113,990 B2
(45) Date of Patent: Oct. 30, 2018

(54) MICROBIAL SENSOR SYSTEM FOR THE ASSESSMENT OF SUBSURFACE ENVIRONMENTS

(71) Applicants: Scott R. Burge, Tempe, AZ (US); Russell G. Burge, Mountain View, CA (US); David A. Hoffman, Tempe, AZ (US)

(72) Inventors: Scott R. Burge, Tempe, AZ (US); Russell G. Burge, Mountain View, CA (US); David A. Hoffman, Tempe, AZ (US)

( * ) Notice: Subject to any disclaimer, the term of this patent is extended or adjusted under 35 U.S.C. 154(b) by 179 days.

(21) Appl. No.: 15/237,230

(22) Filed: Aug. 15, 2016

(65) Prior Publication Data

US 2017/0045470 A1 Feb. 16, 2017

Related U.S. Application Data

(60) Provisional application No. 62/205,254, filed on Aug. 14, 2015, provisional application No. 62/263,362, filed on Dec. 4, 2015, provisional application No. 62/308,680, filed on Mar. 15, 2016.

(51) Int. Cl.
*G01N 27/327* (2006.01)
*G01N 27/416* (2006.01)
*G01N 27/403* (2006.01)

(52) U.S. Cl.
CPC ..... *G01N 27/4163* (2013.01); *G01N 27/4035* (2013.01); *G01N 27/327* (2013.01)

(58) Field of Classification Search
CPC .................................. G01N 27/327–27/3278
USPC ...... 204/409–412, 403.01–403.15, 416–420; 435/34–40, 287.1–288.7
See application file for complete search history.

(56) References Cited

U.S. PATENT DOCUMENTS 5,254,461 A * 10/1993 Rohrback ................ C12O 1/06
205/777.5
5,487,981 A * 1/1996 Nivens ..................... C12Q 1/04
205/777.5

* cited by examiner

*Primary Examiner* — Bach T Dinh
(74) *Attorney, Agent, or Firm* — Snell & Wilmer L.L.P.

(57) ABSTRACT

A microbial sensor, system, and method that can be used to determine a chemical environment and/or substrate concentrations in anaerobic or aerobic environments, such as soils, sediments and ground waters, are disclosed. An exemplary system uses one or more (e.g., inert) measurement electrodes and a reference electrode. The reference electrode can include an electrode exposed to atmospheric oxygen (e.g., a cathode) or an electrode exposed to stable anaerobic or aerobic conditions. The exemplary microbial sensor system measures open-circuit voltage to characterize the chemical (oxidizing or reducing) environment and/or recovery voltage to measure substrate concentrations in the subsurface.

20 Claims, 8 Drawing Sheets

MICROBIAL SENSOR SYSTEM FOR THE ASSESSMENT OF SUBSURFACE ENVIRONMENTS

CROSS REFERENCE TO RELATED APPLICATION

This application claims the benefit of U.S. Provisional Application No. 62/205,254, filed Aug. 14, 2015, entitled "Microbial Sensor System for the Assessment and Remediation of Environmental Contamination in Anaerobic Environments"; Provisional Application No. 62/263,362, filed Dec. 4, 2015, entitled "Field-Deployable Microbial Fuel Cell Sensor System for the Characterization of Environmental Contamination in Aerobic and Anaerobic Environments"; Provisional Application No. 62/308,680, filed Mar. 15, 2016, entitled "Field-Deployable Microbial Fuel Cell Sensor System for the Characterization of Environmental Contamination in Aerobic and Anaerobic Environments," the contents of which are incorporated herein by reference to the extent such contents do not conflict with the present disclosure.

STATEMENT REGARDING FEDERALLY SPONSORED RESEARCH OR DEVELOPMENT

This invention was made with government support by the Office of Science grant DE-FOA-0001405 awarded by the Department of Energy. The government has certain rights in the invention.

FIELD OF INVENTION

The present disclosure generally relates to microbial sensors, systems, and to methods of using the sensors and systems. More particularly, the present disclosure relates to sensors and systems that employ open-circuit voltage and/or recovery voltage measurements to provide information regarding microbial activity.

BACKGROUND OF THE DISCLOSURE

Microbial fuel cells were developed primarily for the conversion of waste products (sewage, farming wastes, etc.) into electrical energy. However, other applications of microbial fuels cells include use as analytical sensors and bioremediation. The primary difference in the microbial fuel cells for energy production and/or bioremediation applications versus the analytical applications is the magnitude of the current generated. Energy production and bioremediation application generally require anodes and cathodes with large surfaces to increase the production of current, whereas high current is not of primary importance for analytical sensor applications.

Microbial fuel cell technology can be roughly divided into two basic types of designs: 1) reactor designs, and 2) probe designs. The two designs have been used for energy production, bioremediation, and analytical applications. The differences between the two designs are based on: 1) the placement and orientation of the anode and cathode, 2) method of substrate (oxidizable organic materials) introduction to the anode, and 3) the method of providing the ultimate electron acceptor (e.g., oxygen, ferricyanide, and the like) to the cathode.

Reactor Designs

A reactor design typically incorporates the anode inside of an anode chamber where the wastewater or natural waters are flowed through the chamber. The cathode design is considerably more varied and includes: 1) air cathodes, 2) cathodes located in a separate cathode chamber, and 3) poised electrodes. Air cathodes are incorporated into the wall of the anode chamber and allow the diffusion of atmospheric oxygen through a semi-permeable membrane to a cathode located within the anode chamber. Cathodes located in a separate cathode chamber are separated from the anode chamber using a semi-permeable membrane. The cathode chamber is typically filled with an oxygenated aqueous solution, or alternatively filled with a solution (e.g., ferricyanide) capable of accepting electrons from the anode. The chamber design is used for energy production, bioremediation, and analytical applications.

The reactor design applications for analytical sensor have been primarily limited to applications where high concentrations (e.g., millimolar (mM)) of organic substrates exist in wastewaters and/or sludges associated with sewage plants and solid waste disposal facilities. One significant application for microbial sensors is the determination of biological oxygen demand (BOD) in wastewaters. Microbial sensors designed for the determination BOD of wastewaters typically use a reactor design. Wastewater is transported in pipes at treatment facilities, and therefore it is convenient to divert the flow of the wastewaters through reactors for the measurement of BOD.

Typical BOD sensors measure the electrical current between the anode and cathode (or poised electrode) as the metric for BOD. Disadvantages of such sensors using a reactor design for analytical applications for characterizing submerged sediments and natural waters include:

The reactor design requires the substrate in water to be passed through an anode chamber. This is not a viable option if the anode is being directly inserted in sediments, soils and groundwater.

Reconfiguration of reactor designs to match the actual site conditions is difficult and not suitable for a majority of the sites.

Most reactor designs are optimized (anode and cathode size, microbial composition, and performance) for energy production that is not an important parameter for an analytical sensor.

Reactor design is not convenient for the deployment of multiple sensors to characterize the chemical (oxidizing and reducing) environment of a site.

The sensors rely on current measurement to determine microbial activity/substrate concentration; such current measurement may not be sensitive enough to measure desired microbial activity.

Probe Designs

Probe design generally include separate anode and cathode components that are not placed into chambers. The probes are usually placed into natural environments, or artificial ponds/digesters at wastewater treatment facilities. The anode is placed in either anaerobic sediment in natural environments, or at an anaerobic zone in wastewater treatment ponds/digesters. The cathode is typically placed into an oxygenated zone above the anaerobic zone where the anode is deployed. The probe design is used for energy production, bioremediation, or analytical applications.

Anode and cathode probes are used in the production of electrical power in marine environments. In these cases, the anodic probe is buried in the anaerobic marine sediments and the cathodic probe is positioned above the anaerobic sediments in the oxygenated water. The typical application of these benthic probes is the production of energy for navigation buoys and other marine instrumentation. Benthic probes are primary used for power production and not as analytical sensors.

A probe that uses three electrodes for energy production and organic contaminant removal at wastewater or sewage treatment facilities based on changing conditions of the organic contaminants present in the water is disclosed in U.S. Pat. No. 9,299,999, issued in the name of Chang et al. The three-electrode system was developed for energy production and contaminant removal, not as an analytical sensor. A primary concern of the '999 Patent is the optimization of electrical current in changing environments. The three-electrode system has a floating cathode and an anode placed into the sediment or sludge at the bottom of a digester. The third electrode is located in the water column between the anode and cathode to serve as either and anode or cathode depending on the water conditions.

A BOD analytical system combines the anode and the electron acceptor into the same probe is disclosed in U.S. Pat. No. 6,113,762, issued in the name of Kruber et al. The probe design does not use oxygen as the ultimate electron acceptor, but rather uses a three-electrode system: counter electrode, microbial electrode and reference electrode with a potentiostat.

Microbial fuel sensors have been deployed in the environment to measure microbial activity in groundwater for bioremediation applications. One application deployed an anodic probe within a monitoring well to determine the reduction of uranium (VI) to uranium (IV) at a site located in Rifle, Colo. The cathode was located at the surface of the site. Reagents were injected into the contaminated groundwater to induce the reduction of uranium. The injection of reagents resulted in relatively high substrate concentrations (e.g., on the order of mM) in the aquifer. The electrical current was measured between the anode and cathode as the metric for acetate concentrations. The cathode was placed into an oxidizing environment at ground surface.

A microbial sensor system was used to evaluate the operating characteristics of the system when exposed to very low concentrations (e.g., on the order of micromolar (uM) or nanomolar (nM)) of substrates. The results of the investigation indicated that microbial sensors have environmental applications at low substrate concentrations and/or in the evaluation of turnover rates. The electrical current was measured between the anode and cathode of the system as the metric for substrate concentration. The investigation performed in 2014 and was cited by the authors as being the first investigation of microbial sensors being exposed to very low concentrations of substrates. The anode was placed into the anaerobic zone of the chamber (bottom) while the top zone of the chamber was oxygenated. The cathode was placed into the oxygenated zone. The system was developed to determine if microbial sensors could detect current at very low concentrations in a variety of sediments, not as a practical analytical system that could be deployed in the field.

Below are illustrative disadvantages of the prior art probe designs and methods for analytical applications of characterizing submerged sediments and natural waters.

The probe designs place the anode in the anaerobic zone (sediment or water) but most designs place the cathode in an aerobic zone located above the anaerobic zone within the same pond or test chamber, or at the surface. This limits the ability to deploy the system at sites with completely anaerobic conditions.

The probes designs do allow for reconfiguration of the probes for deployment in a variety of environments including soils, sediments and groundwater.

The systems use measurement of current as the metric of substrate concentration or turn-over rate.

Multiple sensor deployments require using multiple reference electrodes.

The systems require use of a cathode or a poised electrode.

SUMMARY OF THE DISCLOSURE

Various embodiments of the present disclosure relate to methods and systems for characterizing an environment, such as environments thought to be contaminated. While the ways in which various embodiments of the disclosure address the drawbacks of the prior art are discussed in more detail below, in general, the disclosure provides sensors that are relatively sensitive (can detect very low substrate concentrations), have a relatively simple design, have a reconfigurable design—allowing for use of the sensor in a wide variety of applications, and/or can have a relatively long lifetime in the environment, systems including the sensors, and methods of using the sensors and systems.

In accordance with various embodiments of the disclosure, a microbial sensor system includes a cathode assembly comprising a cathode in a first environment, a conduit coupled to the cathode assembly, the conduit configured to expose the cathode to a second environment, one or more anodes in the first environment, and a device (e.g., a device that is part of a measurement and/or control/communication module) capable of characterizing the first environment by measuring one or more of an open circuit voltage between the anode and the cathode and a recovery voltage between the cathode and anode, the device coupled to and interposed between the cathode and the one or more anodes. In accordance with various aspects of these embodiments, the open circuit voltage is used to characterize or determine a chemical environment near the anode. For example, a measurement or measurements of the open circuit voltage can be used to determine whether the first environment is aerobic or anaerobic, and substrate concentrations in the first environment. In accordance with additional aspects, the recovery voltage can be used to characterize or determine a substrate concentration in the first environment. In accordance with further aspects, the microbial sensor system further includes a float coupled to the cathode.

In accordance with further exemplary embodiments of the disclosure, a microbial sensor system includes one or more measurement electrodes in an environment, a reference electrode in the environment, and a device capable of characterizing the environment by measuring one or more of an open circuit voltage between the reference electrode and each of the one or more measurement electrodes, and a recovery voltage the between the reference electrode and each of the one or more measurement electrodes, the device coupled to and interposed between the reference electrode and the one or more measurement electrodes. In accordance with some aspects of these embodiments, the reference electrode can include an inert electrode or the most stable electrode.

In accordance with further exemplary embodiments of the disclosure, a microbial monitoring system includes a cathode assembly comprising a cathode and a permeable membrane, a conduit coupled to the cathode assembly, the conduit configured to provide access to a second environment when the cathode assembly is submerged in a first environment, an anode, and a device interposed between the anode and the cathode, the device capable of measuring one or more of an open circuit voltage and a recovery voltage between the anode and the cathode to characterize the first environment.

Exemplary systems described herein can additionally include calibration module(s), temperature sensors, and/or various connectors.

In accordance with additional embodiments of the disclosure, a method of measuring microbial activity in an environment or otherwise characterizing the environment includes providing a reference electrode in the environment, providing one or more measurement electrodes in the environment, and measuring one or more of an open circuit voltage between the reference electrode and the one or more measurement electrodes and a recovery voltage between the reference electrode and the one or more measurement electrodes to characterize the environment. In accordance with some aspects of these embodiments, the reference electrode can include an inert electrode or the most stable electrode. Exemplary methods additionally include measuring a current between a reference electrode and a measurement electrode.

BRIEF DESCRIPTION OF THE DRAWING FIGURES

A more complete understanding of exemplary embodiments of the present disclosure may be derived by referring to the detailed description and claims when considered in connection with the following illustrative figures.

Figure 1:
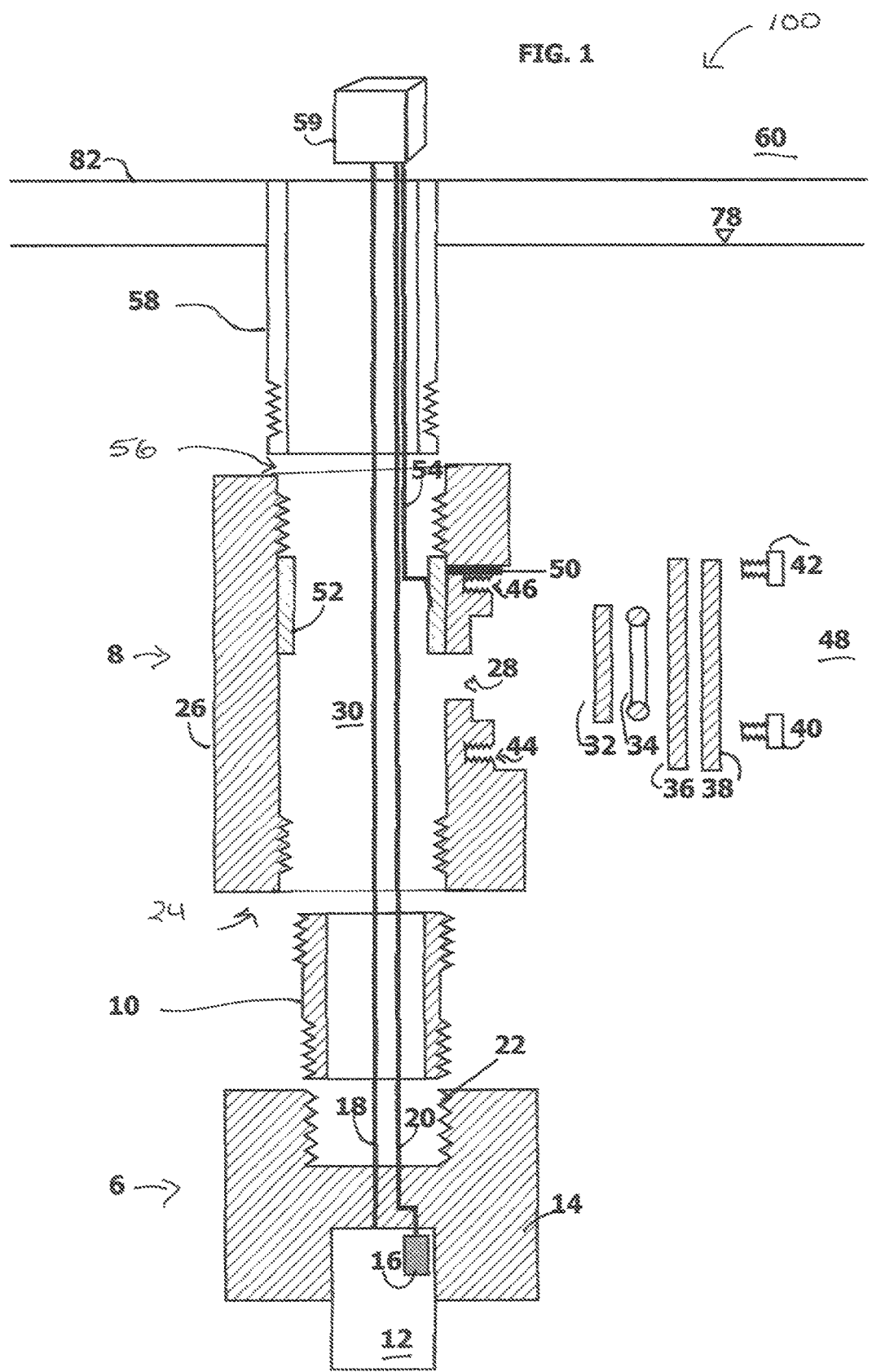
FIG. 1 illustrates a system including anode and cathode assemblies in accordance with at least one embodiment of the disclosure.

It will be appreciated that elements in the figures are illustrated for simplicity and clarity and have not necessarily been drawn to scale. For example, the dimensions of some of the elements in the figures may be exaggerated relative to other elements to help to improve understanding of illustrated embodiments of the present disclosure

DETAILED DESCRIPTION OF EXEMPLARY EMBODIMENTS OF THE DISCLOSURE

The description of exemplary embodiments of methods, systems, and probes provided below is merely exemplary and is intended for purposes of illustration only; the following description is not intended to limit the scope of the disclosure or the claims. Moreover, recitation of multiple embodiments having stated features is not intended to exclude other embodiments having additional features or other embodiments incorporating different combinations of the stated features.

As noted above, prior microbial sensor technologies (energy production, bioremediation, analytical sensors) are primarily based on the measurement of electrical current between an anode and a cathode. The measurement of constant current allows for the determination of substrate concentration in a solution. In contrast, the inventors surprisingly found that measurements of open-circuit voltage (OCV) and recovery voltage (RV) are capable of providing information distinct from the measurement of constant current and can use less sensitive instrumentation to provide meaningful information regarding substrates and concentrations thereof that are or may be present in an environment.

Furthermore, the prior-art techniques generally do not address designs and methods for deployment of microbial sensors in the environment including:

Applications where the cathode is deployed below the static water level in anaerobic environments (groundwater and submerged soils).

One cathode (serving as a reference electrode) to evaluate open-circuit voltages of multiple anodes deployed in the environment.

The use of an alternative reference electrode (as a replacement of the cathode requiring atmospheric oxygen) to evaluate the open-circuit voltages of multiple anodes deployed in the environment. The reference electrode can have the same design as the anodes, but is located in a stable anaerobic environment.

Use of open-circuit voltage as a metric for determination of the chemical (oxidizing/reducing conditions) environment of submerged soils/sediments and ground waters.

Use of recovery voltage as a metric for the determination of substrate concentrations and/or turn-over rates in submerged soils/sediments and ground waters.

Various embodiments of the present disclosure include such designs and, to the extend not inconsistent with this disclosure, combinations of such designs.

The present disclosure relates generally to fuel cell technology being used in analytical sensors to determine the chemical (oxidizing or reducing) characteristics and substrate concentrations in environments, such as saturated sediments and ground waters. Exemplary sensor systems can be incorporated into a probe to allow for deployment at a variety of environmental sites. The design of the exemplary sensor systems described herein can allow for at least three different electrical measurements to be performed: current, recovery voltage and open-circuit voltage. Additionally, various embodiments of the disclosure relate to an (e.g., automated) system for performing the electrical measurements. Such systems may be further be configured to communicate the data to remote users. Aspects of exemplary sensor systems include:

Anode/cathode probe design capable of reconfiguration depending on the characteristic of the site/environment (soils, sediments and groundwater).

Cathode design allowing for exposure of the cathode to atmospheric oxygen when the cathode is submerged in anaerobic groundwater or saturated sediments/soils.

A monitoring system design that includes a device allowing for one cathode (reference electrode) and one or more anodes (measurement electrodes) for characterizing the chemical (oxidizing/reducing) environment of the subsurface.

A monitoring system design that includes a device allowing for an alternative reference electrode and one or more measurement electrode for characterizing the chemical (oxidizing/reducing) environment of the subsurface.

An anode located within a calibration chamber or module allowing the capture of metabolic gases for the calibration of the microbial sensor.

Figure 6:
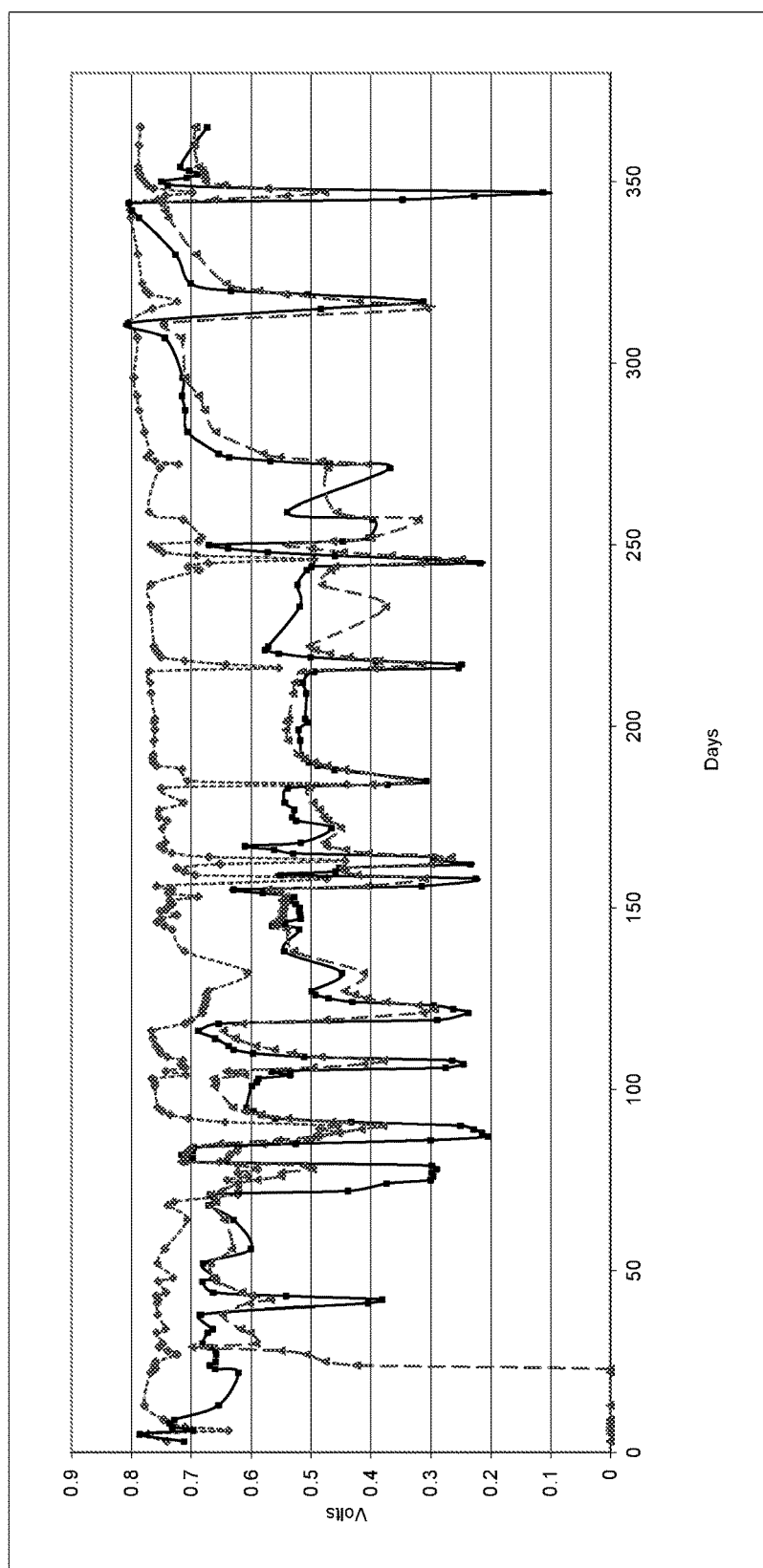
FIG. 6 is a graph illustrating open circuit voltage measurements over time using an exemplary system of the disclosure.

Measurement of open circuit voltage as a metric for the determination of the chemical (oxidizing and reducing) environment being monitored by the microbial sensing system. (FIG. 6).

Figure 7:
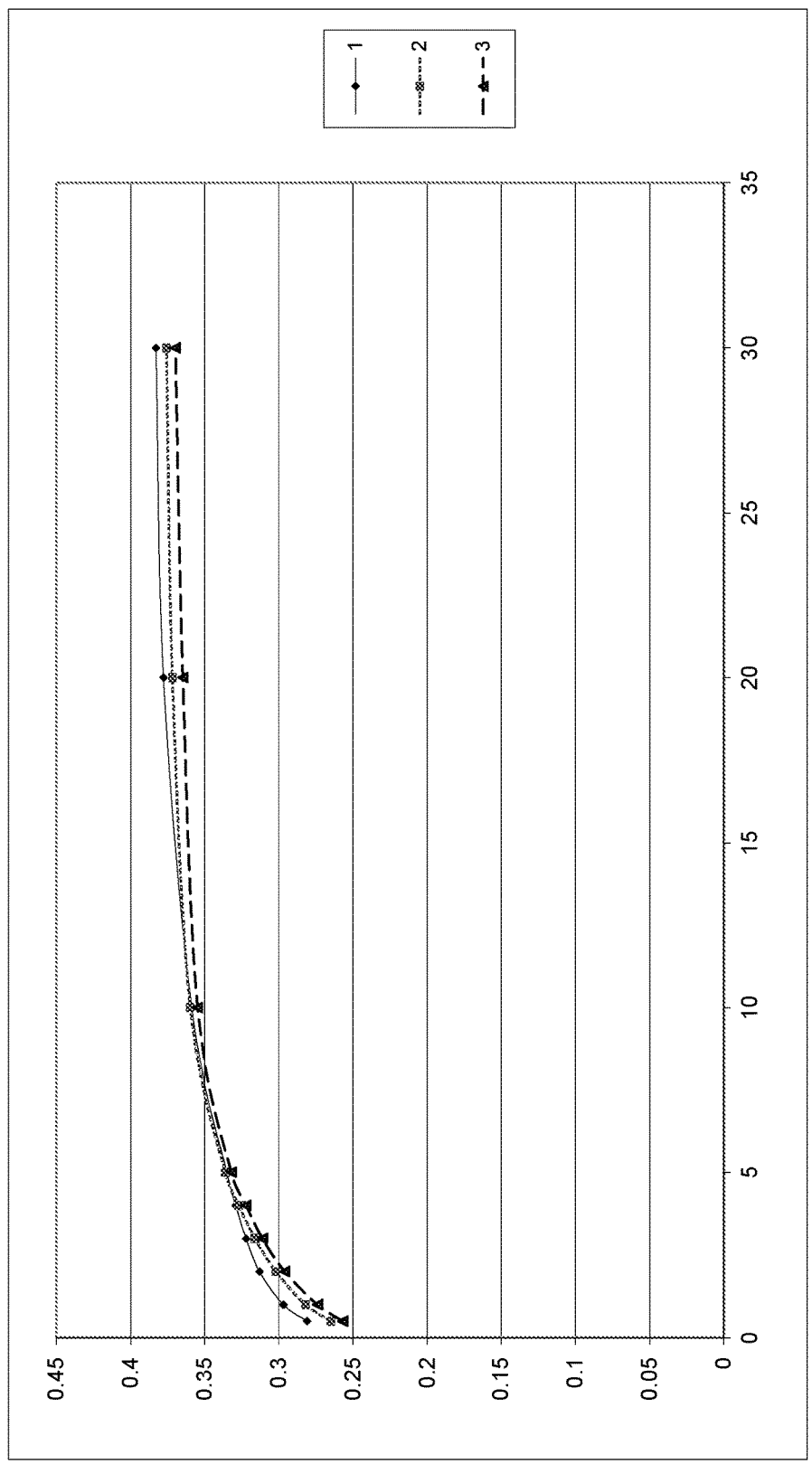
FIG. 7 is a graph illustrating recovery voltage over time as measured using a system in accordance with exemplary embodiments of the disclosure.
Figure 8:
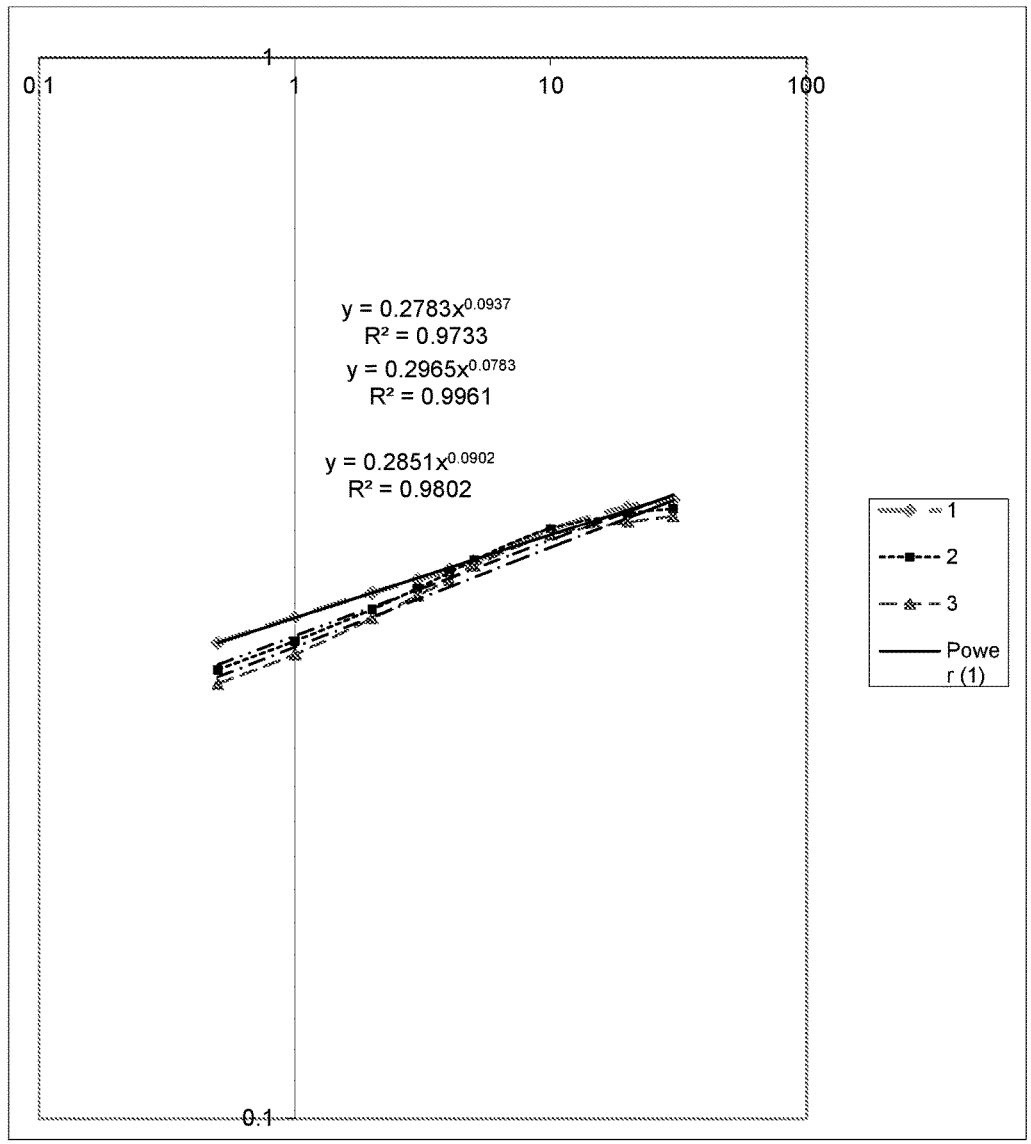
FIG. 8 is a log-log graph further illustrating the recovery voltage over time data illustrated in FIG. 7.

Measurement of the recovery voltage as a metric for the determination of the substrate concentration, or substrate turn-over rate. (FIGS. 7 and 8).

The sensor system may be employed in several different environments for a variety of scenarios including:

Remediation/Monitoring: The system can be used to characterize contaminated (anaerobic) environments to determine the efficiency of a remedial action.

Long-Term Monitoring: The system can be used for assessing passive (Natural Zone Source Depletion) remediation projects, or serve as a method for assessing Monitored Natural Attenuation (MNA) where active remediation has been terminated.

Sentinel Monitoring: The system can be deployed in uncontaminated (aerobic) environments (e.g., aquifers) to determine if the aquifer was impacted by a release of environmental contamination (i.e. petroleum fracking operations, landfills). The presence of oxidizable environmental contaminants will cause natural waters to change from aerobic to anaerobic conditions creating a measurable voltage.

Sensor Measurements

The measurement of OCV provides a very different characterization of an environment surrounding the anode, or measurement electrode, than the measurement of electrical current. The OCV mode of operation requires that no or an immeasurable amount of electrons (or electrical current) flow between the anode and cathode. (FIG. 6). The OCV measurement is used for the determination of the reduction/oxidation conditions, and not the substrate concentration of the solution. The difference between the OCV and current measurements is best explained by the response of the microbes to either: 1) a flow of electrons generated by the oxidation (source of electrons) of substrates at the anode and the flow of electrons to the cathode (the electron acceptor), or 2) the scenario where no electrons are allowed to flow from the anode to the cathode.

Certain types of microbes (e.g., *Geobacter* sp.) are attracted to and attach to the anode. The microbes form a biofilm that connects the cells to the anode. The microbes can use several types of mechanisms to pass the electrons from the microbe to the anode through the biofilm. The electron transfer methods include nanowires, cytochromes and mobile shuttles. If electrons are allowed to flow from the anode to the cathode, the electrons produced during the oxidation of the substrates use the electron transfer mechanisms and the flow of current is a metric for the substrates oxidized by the microbes. The magnitude of the electrical current may be in the lower microampere ($\mu A$) to nanoampere (nA) range for solutions with low substrate concentrations.

However, if the flow of current is terminated between the anode and cathode, the microbes begin to store the electrons generated by the oxidation of the substrate in temporary electron acceptors such as cytochromes. The cytochromes are located internal or external of the microbes. The cytochromes located external of the microbes are embedded in the biofilm. The OCV increases between the anode and the cathode as the charge stored in the cytochromes increases. Voltages (OCV) of up to 0.9 Volts are observed between an anode located in (e.g., completely) anaerobic conditions and a cathode exposed to atmospheric oxygen. The microbes continue the metabolism of the substrates and transfer the charge into the temporary electron acceptors until the transfer of charge is no longer thermodynamically favorable. The microbes will maintain the voltage between the anode and cathode until either 1) the flow of current is reestablished between the anode and cathode discharging the stored charge, or 2) an alternative electron acceptor is present in the solution discharging the charge stored in the temporary electron acceptors (cytochromes).

Generally, the most significant electron acceptor that may be present in an environment is dissolved oxygen. If the concentration of dissolved oxygen increases in the solution surrounding the anode, the stored charge is transferred from the cytochromes to the dissolved oxygen. The transfer of charge from the temporary electron acceptors in the microbes and surrounding biofilm to the dissolved oxygen results in a decrease of the OCV measured between the anode and cathode. (FIG. 6). The OCV is low in aerobic conditions and significantly higher is anaerobic conditions. If dissolved oxygen is removed from the solution and anaerobic conditions reestablished, the charge in the cytochromes increases with a corresponding increase in the OCV. Therefore, the OCV is a metric for the chemical (reduction/oxidation) environment of the solution. This is a quite different than the estimate of substrate concentration that is measured by the flow of current between the anode and cathode.

Two primary problems are encountered with the measurement of constant current between the anode and cathode as a metric for determining substrate concentrations, or turn-over rates (at very low concentrations). The two problems are: 1) the increase in the internal resistance of the electrochemical cell over time, and 2) the complexity of the measurement circuitry required for the measurement of very low electrical currents. An increase in the internal resistance between the anode and cathode is observed over time when measuring constant currents. This results in a long-term drift of the signal toward lower currents. An analytical system that varies over time is difficult to use, unless a method of calibration can be devised to account for the changing signal. Because most of the measurements envisioned to be performed by the analytical system are at the level of the turn-over rates, the introduction of calibration standards is not appropriate. One method of calibration, in accordance with the present disclosure, is the measurement of metabolic gases ($CO_2$) produced at the anode by microbes (e.g., *Geobacter*, sp.).

In accordance with various embodiments of the disclosure, a method of determining substrate concentration, or turn-over rates, uses recovery voltages as opposed to the measurement of constant current. The use of recovery voltage has two primary advantages including 1) changes in internal resistance appear to be less of a factor, and 2) the measurement of voltages—e.g., in the range of 0.3 to 0.6 Volts uses less complex circuitry than used in the measurement of the low currents (uA to nA). However, the measurement of recovery voltage is a kinetic measurement and the data analysis of recovery voltage is more complex than the measurement of constant current.

The measurement of recovery voltage includes a three-step process. The first step allows the OCV to stabilize. The second step uses a temporary discharge of the charge stored in the cytochromes. The third step uses the termination of the temporary discharge of charge, and a record of the increase of voltage over time as the cytochromes recover the charge lost in the second step.

During the first step, the OCV stabilizes at a constant or preset voltage. In anaerobic conditions, the voltage will typically stabilize between 0.5 to 0.8 Volts.

After the OCV stabilizes, the second step allows the flow of electrical current between the anode and cathode for a period of time. The flow of current partially discharges the charge stored by the cytochromes. One to ten minutes is typical period of time to flow the current between the anode and cathode. The voltage between the anode and cathode drops significantly (e.g., 0.2 to 0.5 Volts) when the current flows between the anode and cathode.

After the period to time, the third step terminates the flow of current between the anode and cathode. After the flow of current is terminated, the OCV increases. The OCV voltage versus time curve generated is similar in characteristics to the voltage-time curve generated during the charging of a capacitor, as illustrated in FIG. 7. The charge stored under the voltage-time curve is directly related to the electrons generated from the oxidation of substrates. Therefore, the generation and measurement of the recovery voltage may be used to determine either substrate concentration or turn-over rate (at lower concentrations).

Sensor Design

The microbial fuel cell designs for the production of energy are typically optimized for the production of electrical current. The optimization of electrical current includes increasing surface areas of the anode and cathode, flow-though reactors to increase the substrate concentrations exposed to the anode and other factors to increase the production of electrical current In contrast to the measurement of BOD at treatment facilities where the water is transported in pipes, most environmental monitoring is performed by the insertion of probes or sensors directly into an environment, such as soils or into groundwater monitoring wells. Therefore, for these applications, microbial sensors are desirably configured as probes and have the flexibility to be deployed in a variety of natural environments including soils, sediments and natural waters.

In accordance with various embodiments of the disclosure, a cathode can be submerged in anaerobic (e.g., soil and groundwater) environments. Systems for introducing atmospheric oxygen to the cathode, when the cathode is exposed to submerged anaerobic environments, include a conduit or passage through the interior of the probe allowing the introduction of atmospheric oxygen to the cathode. In these cases, an interior of a probe can be hollow and a cathode assembly can be fabricated into a port located in the wall of the probe. The cathode port is located below the static water level. Atmospheric oxygen passes from the atmosphere through a conduit tube (or "snorkel") into the hollow interior of the cathode probe. The cathode assembly is typically composed of a polymer membrane and a cathode. The cathode is typically a platinum impregnated carbon cloth. The polymer membrane of the cathode assembly can perform two tasks: 1) prevent water from entering the interior of the probe, and 2) allow oxygen present in the interior of the cathode probe to diffuse through the polymer membrane to the cathode exposed to anaerobic environment, i.e. groundwater. Additionally or alternatively, a waterproof film or layer may be applied to the cathode cloth.

Because of the myriad of potential environmental applications to monitor soils and ground waters, the positional relationship of the anode and cathode may be changed based on a particular application. The flexibility of the various probes and systems described herein allows for connection of the anode and cathode (or reference and measurement electrodes) to alternative deployment assemblies including floats for monitoring wells. The anode/cathode/electrode connectors include pipe threads, other quick disconnect connectors, and the like.

Two situations illustrating the desire for flexibility in assembling anode and cathode (or, generally electrodes) for deployment in the field include 1) direct insertion probes for monitoring soils, and 2) deployment of the anode and cathode (electrodes) in monitoring wells. The first application allows an anode to be directly connected to a cathode. The assembled probe may be directly inserted into the submerged soil/sediments. The second application allows for the monitoring of groundwater. The cathode is connected to floating module located at the static water level within the interior of the well while the anode is located at a submerged location below the floating module within the well. The cathode assembly connects to the floating module and this connection insures the cathode is both submerged below the static water level, and that the cathode has a direct conduit or snorkel to atmospheric oxygen.

The measurement of OCV, as opposed to electric current, allows for a sensor design using one cathode as a reference electrode and one or more anodes as measurement electrodes. The deployment of multiple sensor arrays allows for the characterization the chemical (aerobic/anaerobic) conditions of a site. (FIG. 6). The measurement is made possible because no current flows between the electrodes in the system.

The OCV mode of operation in accordance with various embodiments of the disclosure allows for use of alternative reference electrodes in lieu of a cathode. The cathode is defined as a reference electrode exposed to an oxidizing environment, such as oxygen present in air as the ultimate electron acceptor. For example, if three anodes in an environment are measured against a common cathode in the OCV mode of operation, three different voltages are measured (Table 1). In the example below, anode #3 is the located in the deepest location of test chamber and therefore is located in the most anaerobic conditions.

TABLE 1

| Anode #1 | Anode #2 | Anode #3 |
|----------|----------|----------|
| .397 volts | .321 volts | .713 volts |

If it is determined that voltage of Anode #3 is not likely to change during the timeframe of an investigation of a site, Anode #3 may be selected as an alternative reference electrode because it is located in a stable anaerobic location. If Anode #3 is selected as the reference electrode, the OCV of two remaining anodes are measured against Anode #3 (Table 2).

TABLE 2

| Anode #1 | Anode #2 | Anode #3 |
|---|---|---|
| .316 | .392 | NA |

Therefore, the cathode (electrode exposed to oxygen, aerobic conditions) is replaced as the reference electrode with Anode #3 exposed to stable anaerobic conditions, the alternative reference electrode. The replacement of the reference electrode results in a similar characterization of the site in determining the chemical (reducing or oxidizing conditions) environmental of the site. However, the replacement of the cathode as the reference electrode results in the characterization of the site using a much simpler analytical system. Because the cathode is typically the most complex component of a sensor array, its elimination increases the life expectancy of the sensor array. The alternative electrode can be an inert electrode (inert with regard to the surrounding environment) composed of, for example, graphite or other conducting material not corroded in the environment. The design of the alternative reference electrode can be similar to or the same as the anode design.

Referring to the drawing figures, FIG. 1 illustrates, in cross-sectional view, an exemplary microbial sensing system 100 in accordance with at least one embodiment of the disclosure. An anode assembly 6 includes an inert anode 12 connected to an anode body 14. The inert anode 12 can be composed of, for example, graphite or other conducting material—e.g., that does not corrode in the environment in which the anode is inserted. The anode body 14 is composed of a polymer or other non-conducting material not corroded in the environment the anode body 14 is inserted. A temperature probe (or sensor) 16 is embedded within the inert anode 12. The temperature probe 16 may be a thermocouple, thermistor, or RTD. An anode cable 18 electrically connects to the anode 12. A temperature probe cable 20 electrically connects to the temperature probe 16. An anode connection port 22 is located at the terminal end of anode body 14 allowing the connection with an anode connector 10. The anode connector 10 is a hollow tube with a method of connection to the anode connection port 22. The method of connection can include, for example, threads or other type of quick-disconnect fittings. The anode connector 10 allows the passage of the anode cable 18 and the temperature cable 20 from the anode assembly 6 to a cathode assembly 8. The anode connector 10 is composed of a polymer or other non-conducting material not corroded in the environment the anode connector 10 is inserted.

The anode connector 10 connects to a lower cathode connection port 24 located at the terminal end of a cathode body 26. The cathode body 26 is composed of a polymer or other non-conducting material not corroded in the environment the cathode body 26 is inserted. An interior 30 of the cathode body 26 is a hollow tube allowing the passage of the anode cable 18 and the temperature cable 20 through the cathode assembly 8.

A cathode mounting port 28 passes through the cathode body 26 and connects the hollow interior 30 to an exterior environment 48. The cathode mounting port 28 is fitted with a gas-permeable membrane 32. The gas-permeable membrane 32 is composed of a polymer film or other material selected to allow the diffusion of oxygen through the membrane and prevent the introduction of water into the hollow interior 30. An O-ring 34 is fitted over the permeable membrane 32. A cathode 36 and a cathode frame 38 are fitted over the O-ring 34. Mounting screws 40, 42 secure the cathode frame 38 and the cathode 36 to the cathode body 26 using the mounting screw holes 44, 46 in the cathode body 26. The mounting screws 40, 42 are used to apply pressure on the O-ring 34 to create a water-tight seal between the O-ring 34 and the gas-permeable membrane 32 preventing water from entering the hollow interior 30 of the cathode body 26.

The cathode 36 is composed of a platinum-coated carbon fabric or other material capable of reducing molecular oxygen with the electrons generated at the anode 12. The cathode frame 38 is composed of a polymer or other non-conducting material not corroded in the environment the cathode frame 38 is inserted.

A cathode wire 50 passes through the wall of the cathode body 26 and electrically connects the cathode 36 with a conductive collar 52 located within the hollow interior 30 of the cathode body 26. A cathode cable 54 connects to the conductive collar 52.

An upper cathode connection port 56 is located at the terminal end of the cathode body 26 connects with a snorkel (also referred to herein as conduit) 58. The snorkel 58 is a hollow tube with a method of connection to the upper cathode connection port 56. The method of connection includes threads or other type of quick-disconnect fitting. The snorkel 58 allows the passage of the anode cable 18, temperature cable 20 and the cathode cable 54 from the cathode assembly 8 to the atmosphere 60. In addition, the snorkel 58 provides a conduit for oxygen from the atmosphere 60 to diffuse into the hollow interior 30 of the cathode body 26. The oxygen in the hollow interior 30 diffuses through the gas-permeable membrane 32 to the cathode 36. The snorkel 58 is composed of a polymer or other non-conducting material not corroded in the aqueous environment 48 (the environment in which the measurement electrodes are placed is also referred to herein as a first environment. The anode cable 18, temperature cable 20, and the cathode cable 54 connect to a measurement module 59, which can include a device to measure OCV and/or RV, and optionally current as described herein. The device can include one or more circuits.

In the operation of the illustrated system, selected species of bacteria, such as *Geobacter* sp., form biofilms on the surface of the anode 12. The bacteria oxidize various substrates in the aqueous environment 48 and transfer the electrons in the oxidation reaction through the biofilms to the anode 12. The electrons flow from the anode 12 through the anode cable 18 to a measurement module 59 located at ground surface 82. The electrons pass from the measurement module 59 (and the device) through the cathode cable 20 and the conductive collar 52 to the cathode wire 50. The electrons flow through the cathode wire 50 into the cathode 36 located in the aqueous environment 48. The electrons reduce the dissolved molecular oxygen in the aqueous environment 48 to water at the cathode 36. Molecular oxygen serves as the ultimate electron acceptor for the microbial sensor system. If molecular oxygen is not present in the aqueous environment 48 in the vicinity of the cathode 36, an alternative path is provided allowing atmospheric oxygen to be present in the vicinity of the cathode 36. Molecular oxygen diffuses from the atmosphere 60 through the snorkel 58 into the hollow interior 30 of the cathode body 26. The molecular oxygen in the hollow interior 30 of the cathode body 26 diffuses through the gas-permeable membrane 32 to the cathode 36.

In exemplary system 100, the anode assembly 6 and cathode assembly 8 can be quickly reconfigured using the anode connector 3 and the snorkel 58. The anode body 14 has the anode connection port 22 with either threads or other type a quick disconnection. The cathode body 26 has the lower cathode connection port 24 with the threads or other means of quick disconnection. The anode connector 3 has threads or other type of quick disconnection and provides the connection between the lower cathode connection port 24 and the anode connection port 22. The anode connector 10 is hollow to allow the passage of the anode cable 18 and the temperature cable 20 into the hollow interior 30 of the cathode body 26. The design allows different lengths of anode connectors 10 to be inserted or attached. Additionally or alternatively, the anode assembly 6 may be quickly exchanged with different configurations of the anode assembly 6.

The upper terminal end of the cathode body 8 includes the upper cathode connection port 56 with threads or other type of quick disconnect features. The snorkel 58 has a terminal end designed to connect with the threads or other quick disconnect features of the upper cathode connection port 56. The interior of the snorkel 58 is hollow allowing the passage of the anode cable 18, cathode cable 54 and temperature cable 20 from the hollow interior 30 of the cathode body 26 through the snorkel to a measurement module 59 at the surface 82. The design allows the quick and efficient method of reconfiguring the anode assembly 6, cathode assembly 8, and the snorkel 58 into many variants to match the desired configuration for site conditions.

Figure 2:
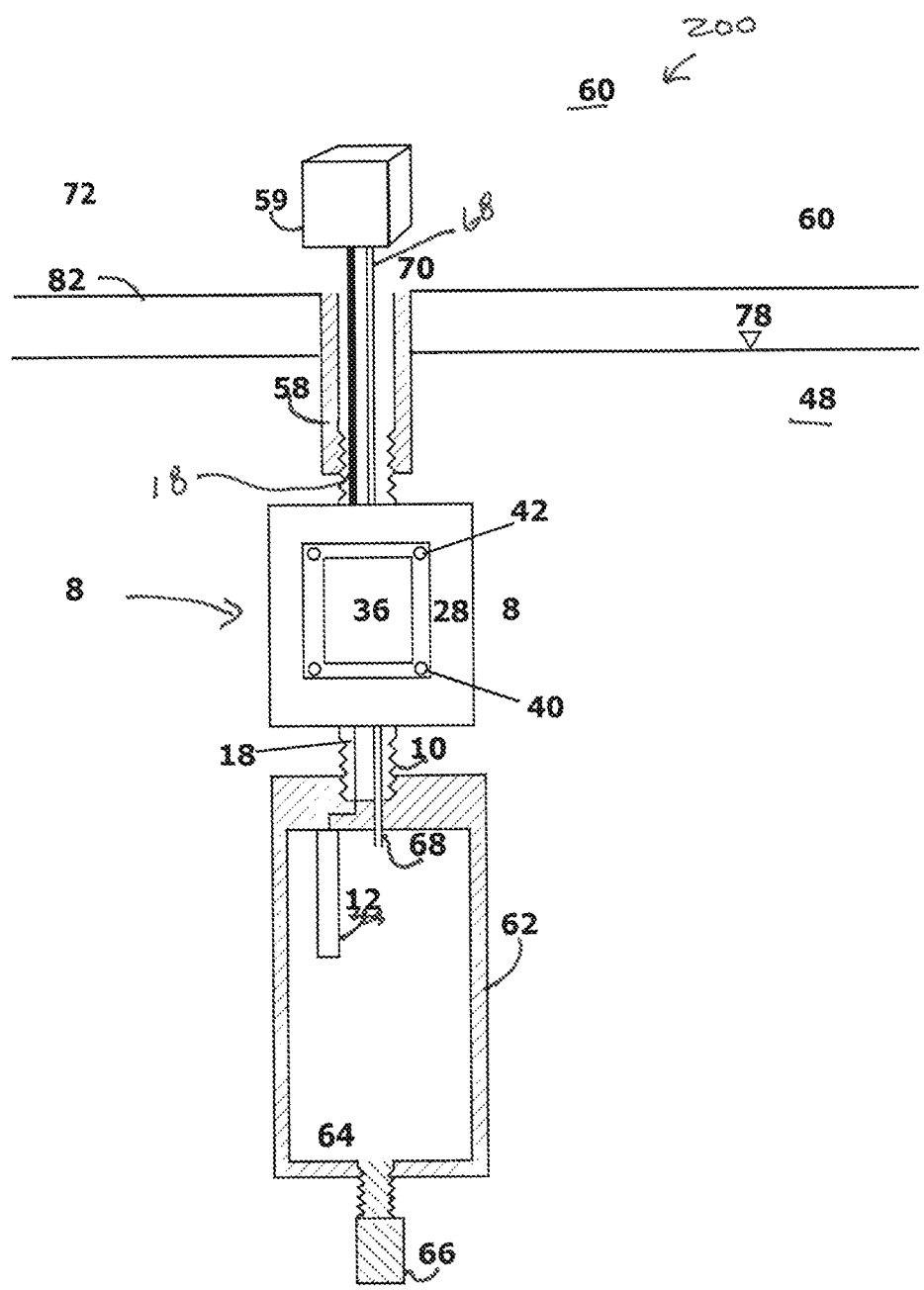
FIG. 2 illustrates another system including anode and cathode assemblies in accordance with at least one embodiment of the disclosure.

FIG. 2 illustrates another exemplary microbial sensor system 200 with an alternative design of the anode assembly. In this embodiment, the anode is located within a calibration chamber or module 62. The system can be formed by reconfiguring a cathode assembly with an alternative design of the anode assembly. Microbial sensor system 200 captures metabolic gases, such as carbon dioxide, generated within a calibration chamber 62, such that microbial sensor system 200 can be calibrated. The calibration chamber 62 is composed of a polymer or other non-conducting material not corroded in the aqueous environment 48. A gas tube 68 is used to remove the metabolic gases generated within the calibration chamber 62. An inert anode 12 is located within the calibration chamber 62. A one-way check valve 66 connects to an entrance port 64 of the calibration chamber 62. The one-way check valve 66 is composed of a polymer or other material not impacted by the (e.g., aqueous) environment 48. The one-way check valve 66 is orientated to allow the flow of water into the calibration chamber 62. The anode connector 10 connects the calibration chamber 62 with the cathode assembly 8. The snorkel or conduit 58 connects to the upper port of the cathode assembly 8. The terminal end of the snorkel 58 is exposed to the atmosphere 60 (e.g., air), also referred to herein as a second environment. The anode cable 18 electrically connects to the anode 12. The anode cable 18 passes through upper wall of the calibration chamber 62, the anode connector 10, the cathode assembly 8, and the snorkel 58 to the measurement module 59. The gas tube 68 passes through the upper wall of the calibration chamber 62, the anode connector 10, the cathode assembly 8, and the snorkel 58 to the atmosphere 60.

The operation of the system 200 is performed by measuring the difference in the carbon dioxide generated within the calibration chamber 62 when current is allowed to flow between the anode 12 and cathode 36 versus when no current is allowed to flow between the anode 12 and cathode 36. The moles of carbon dioxide generated are compared with the number of moles of electrons passing from the anode 12 to the cathode 36.

The carbon dioxide generated accumulates in the calibration chamber 62. The gas tube 68 is used to remove the carbon dioxide gas from the calibration chamber 62 for measurement of the volume of the gas generated within the calibration chamber 62. The withdrawal of the carbon dioxide can be performed using a syringe or other method of collection the gas sample from the calibration chamber 62. The evacuation of the gas from the calibration chamber 62 opens the one-way check valve 66 allowing water 48 to flow into the calibration chamber 62.

Figure 3:
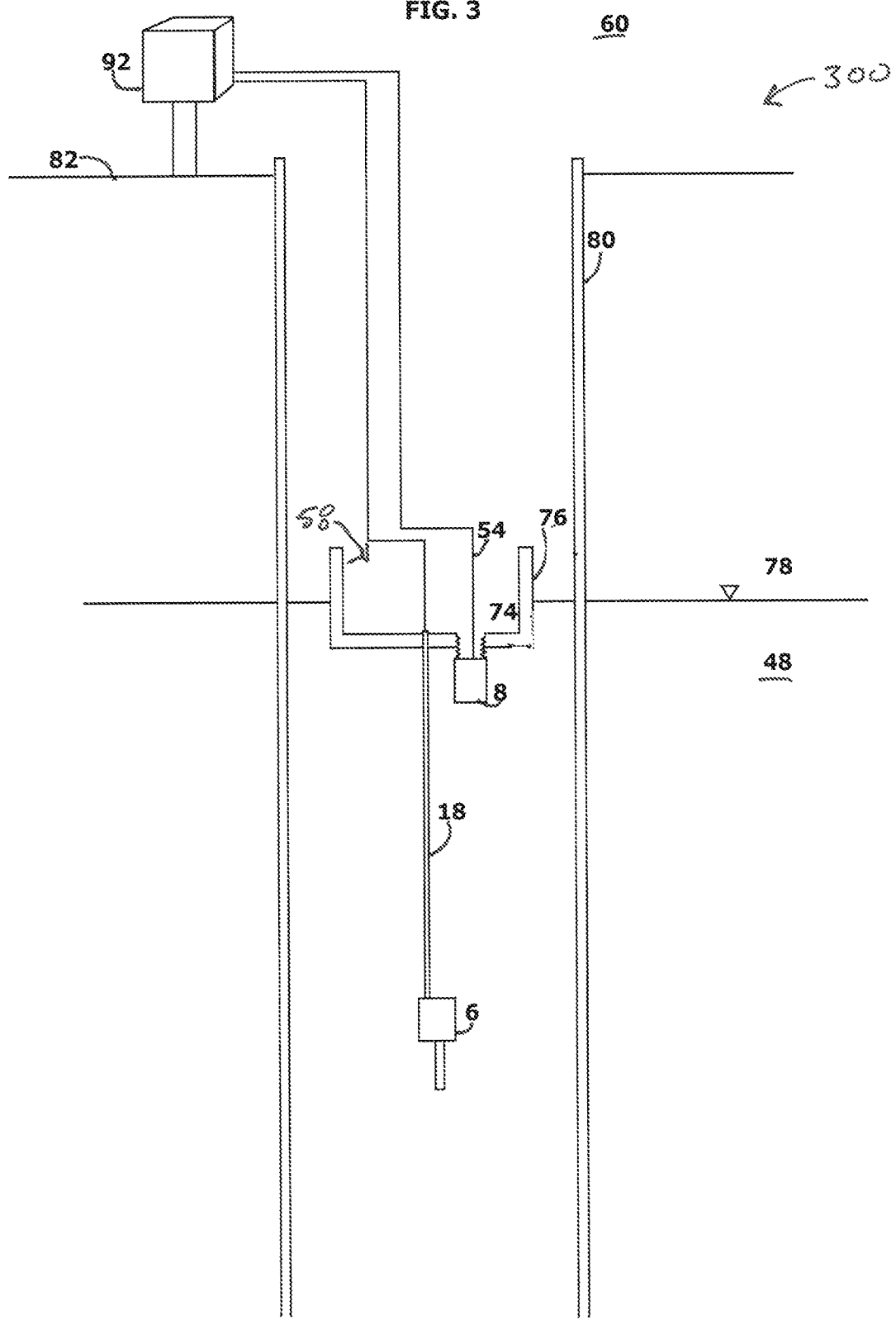
FIG. 3 illustrates an exemplary system deployed within a monitoring well in accordance with yet additional embodiments of the disclosure.

FIG. 3 illustrates another microbial sensing system 300, suitable for deployment in, for example, a monitoring well. Microbial sensing system 300 can be formed by, for example, reconfiguration of the anode and cathode assemblies of microbial sensing system 100. The cathode assembly 8 connects to a float 76 using the snorkel 58. The float 76 is disposed within a well casing 80 to be monitored. The float 76 is located at the static water level 78 within the well casing 80. The float assembly 76 allows oxygen in the atmosphere 60 to diffuse through the snorkel 58 and into the cathode assembly 8. The float 76 is composed of a polymer or other non-conducting material not corroded in the aqueous environment 48. The cathode cable 54 electrically connects to the cathode assembly 8 and passes through the snorkel 58 to a control/communication module 92 located at the surface 82.

In the illustrated example, the anode assembly 6 is located in the aqueous environment 48 below the static water level 78 within the well casing 80. The anode cable 18 electrically connects to the anode assembly 6. The anode cable 18 passes through the float 76 to the control/communication module 92 located at the surface 82.

The operation of the microbial sensing system 300 deployed in a monitoring well can insure that atmospheric oxygen is available to the cathode regardless of the water level with the monitoring well. The anode assembly 6 and cathode assembly 8 are connected to the bottom surface of a float 76. The position of the float 76 within the well casing 80 can depend on the static water level 78 of the aquifer. The vertical movement of the float 76 within the monitoring well facilitates the upper port of the snorkel 58 exposure to the atmosphere 60. The oxygen in the atmosphere 60 diffuses through the snorkel 58 to cathode assembly 8.

The anode assembly 6 suspended below the float 76 can determine a chemical nature or a substrate concentration of the aqueous environment 48. Alternatively, the anode assembly may be deployed within the well casing 80 below the static water level 78 without suspending the anode assembly 6 from the float 76. The electrons, produced by the microbes on the surface by oxidation reaction, from the anode 6, flow through the anode cable 18 to the control/communication module 92. The electrons flow from the control/communication module 92 through the cathode cable 54 to the cathode assembly 8. The flow of electrons is related to the substrate concentration, or turn-over rate, in the vicinity of the anode 6. Alternatively, the current flow between the anode assembly 6 and cathode assembly 8 is terminated and the measurement of the open-circuit voltage is a metric for the chemical environment (oxidizing or reducing) in the vicinity of the anode assembly 6.

Figure 4:
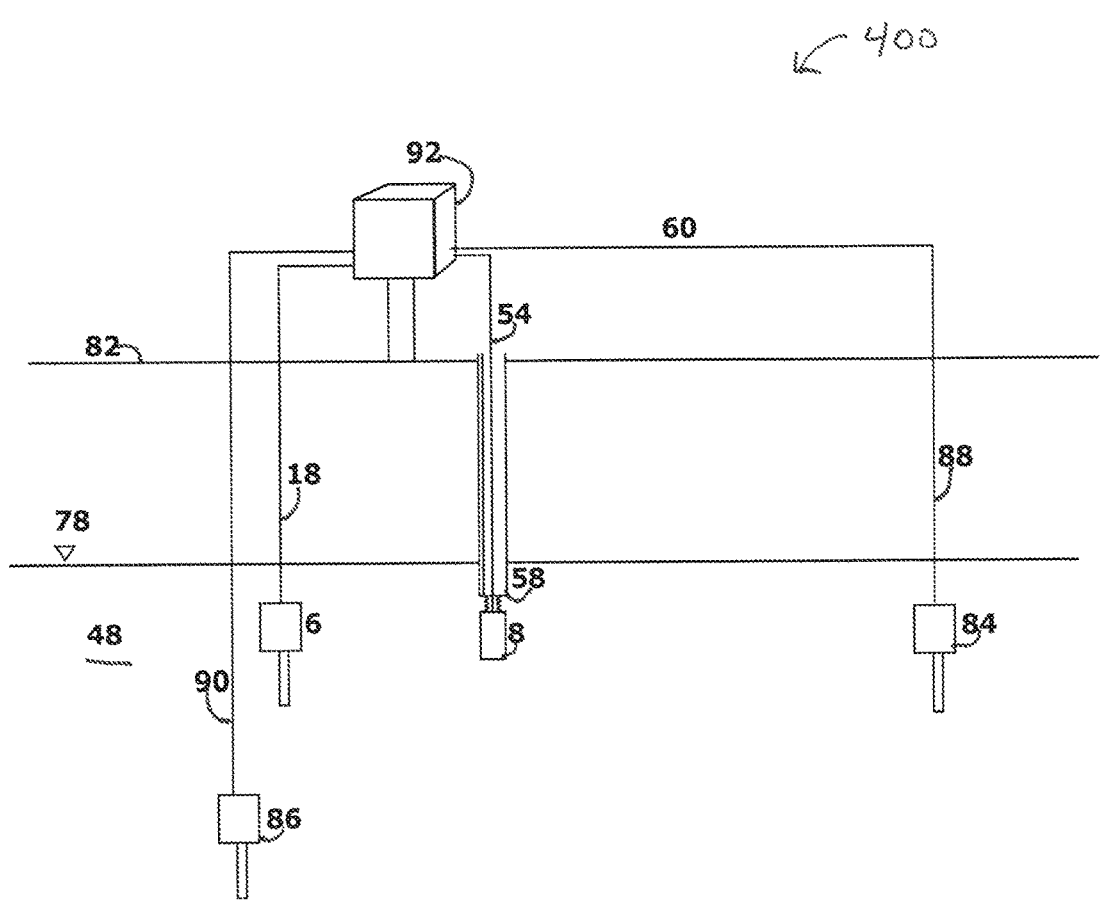
FIG. 4 illustrates a system with one reference cathode and multiple anodes in accordance with at least one embodiment of the disclosure.

FIG. 4 illustrates a multiple microbial sensor network or array 400 with the cathode assembly 8 used as the reference electrode. Several anodes (or measurement electrodes) 6, 84, 86 are located below a static water level 78. The cathode assembly 8 is connected to the snorkel 58. The upper terminal end of the snorkel 58 is exposed directly to the atmosphere 60, or the soil-gas located between the static water level 78 and the ground surface 82. The cathode cable 54 electrically connects the cathode assembly 8 with a control/communication module 92 located at the surface 82. An anode cable 18 electrically connects the anode 18 with the control/communication module 92 located that the ground surface 82.

The operation of network 400 allows a field deployment of multiple anodes using one cathode as the reference electrode to determine the chemical (oxidizing or reduction) environment of a site or an environment. The cathode assembly 8 is located below the static water level 78 in the aqueous environment 48. The snorkel 58 is connected to the cathode assembly 8, allowing the diffusion of oxygen in the atmosphere to reach the cathode assembly 8. A cathode cable 54 connects the cathode assembly with the control/communication module 92 located at ground surface 82. Multiple anodes 6, 84, 86 are placed at different locations within the aqueous environment 48 to be characterized. The anodes 6, 84, 86 are connected with anode cables 18, 88, 90 to the control/communication module 92 located at, for example, ground surface. The open-circuit voltage between the cathode assembly 8 and to each of the anodes 6, 84, 86 is measured to determine the chemical (oxidizing or reducing) nature of the aqueous environment 48 in the vicinity of the anodes 6, 84, 86.

Figure 5:
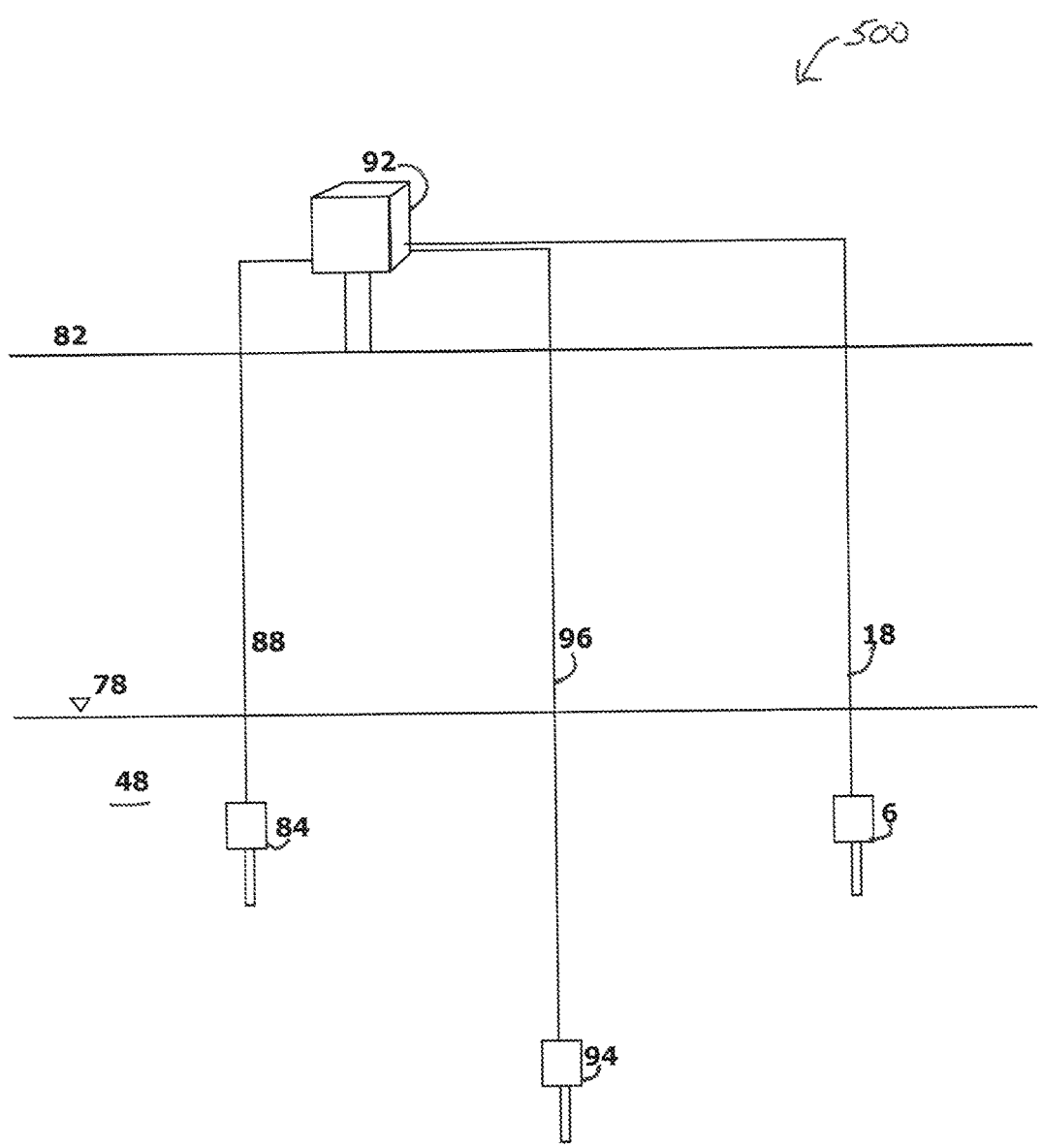
FIG. 5 illustrates yet another system, which includes one alternative reference electrode and multiple measurement electrodes, in accordance with at least one embodiment of the disclosure.

Referring to FIG. 5, a multiple microbial sensor network or array 500, with an inert electrode 94 located in a stable anaerobic location of the aqueous environment 48, is illustrated. If the aerobic conditions are stable in the vicinity of the inert electrode 94, the electrode is used a reference electrode. Multiple anodes 6, 84 are located in the aqueous environment 48 below a static water level 78. An electrode cable 96 electrically connects the inert electrode 94 with the control/communication module 92 located at the surface 82. An anode cable 18 electrically connects the anode 6 with the control/communication module 92 located that the ground surface 82.

The operation multiple microbial sensor network 500 can be employed in a field deployment of multiple measuring electrodes 6, 84 and using an inert reference electrode 94 in determining the chemical (oxidizing or reduction) environment of the site. The reference electrode 94 is placed in an anaerobic location on the site that is not expected to change (or not significantly change) during the course of an investigation. An electrical cable 96 connects the reference electrode with the control/communication module 92 located at, e.g., ground surface 82. Multiple anodes 6, 84 are placed at different locations within the aqueous environment 48 to be characterized. The anodes 6, 84 are connected with anode cables 18, 88 to the control/communication module 92 located at ground surface. The open-circuit voltage between the reference electrode 96 and to each of the anodes 6, 84 is measured to determine the chemical (oxidizing or reducing) nature of the aqueous environment 48 in the vicinity of the anodes 6, 84.

FIG. 6 illustrates OCV versus time for three electrodes (e.g., anodes) disposed within a test chamber, wherein each electrode is at a different level within the test chamber. Oxygen was periodically introduced into the reaction chamber. As the oxygen is introduced, the OCR is reduced, indicating an aerobic environment in the test chamber. Conversely, when nitrogen is introduced into the test chamber, the OCR increases, indicating an anaerobic environment.

FIGS. 7 and 8 illustrate RV measurements in Volts taken from three measurement electrodes versus time in minutes. The RV can be obtained using the techniques described above. FIG. 8 is a log-log plot of the data illustrated in FIG. 7. The area under the curve in FIG. 8 corresponds to a concentration of a substrate in the environment.

The Exemplary systems, probes, and methods have been described above with reference to a number of exemplary embodiments and examples. It should be appreciated that the particular embodiments shown and described herein are illustrative of the invention and its best mode and are not intended to limit in any way the scope of the invention. It will be recognized that changes and modifications may be made to the exemplary embodiments without departing from the scope of the present invention. These and other changes or modifications are intended to be included within the scope of the present invention. Further, the subject matter of the present disclosure includes all novel and nonobvious combinations and subcombinations of the various processes, systems, arrays, and probes, and other features, functions, acts, and/or properties disclosed herein, as well as any and all equivalents thereof.

We claim:

1. A microbial sensor system comprising:
    a cathode assembly comprising a cathode in a first environment;
    a conduit coupled to the cathode assembly, the conduit configured to expose the cathode to a second environment;
    one or more anodes in the first environment; and
    a device capable of characterizing the first environment by measuring one or more of an open circuit voltage and a recovery voltage between the anode and the cathode, the device coupled to and interposed between the cathode and the one or more anodes.

2. The microbial sensor system of claim 1, wherein open circuit voltage corresponds to the chemical environment of the microorganisms in the first environment.

3. The microbial sensor system of claim 1, further comprising a float coupled to the cathode.

4. The microbial sensor system of claim 1, wherein the recovery voltage corresponds to a substrate concentration in the first environment.

5. The microbial sensor system of claim 1, wherein the cathode is a reference electrode.

6. The microbial sensor system of claim 1, wherein the anode comprises one or more of graphite, gold, and platinum.

7. The microbial sensor system of claim 1, wherein the cathode comprises platinum-coated carbon fabric.

8. The microbial sensor system of claim 1, wherein the microbial sensor system comprises a plurality of anodes and the one or more of the open circuit voltage between the anode and the cathode and the recovery voltage of the system are measured between the cathode and each of the plurality of anodes.

9. A microbial monitoring system comprising:
    a cathode assembly comprising a cathode and a permeable membrane;
    a conduit coupled to the cathode assembly, the conduit configured to provide access to a second environment when the cathode assembly is submerged in a first environment;
    an anode; and
    a device interposed between the anode and the cathode, the device capable of measuring one or more of an open circuit voltage and a recovery voltage between the anode and the cathode to characterize the first environment.

10. The microbial monitoring system of claim 9, further comprising a chamber enclosing the anode for the measurement of metabolic gases for the purpose of calibration of the device.

11. The microbial monitoring system of claim 9, further comprising a float coupled to the conduit.

12. The microbial monitoring system of claim 9, wherein the microbial monitoring system comprises a plurality of anodes.

13. The microbial monitoring system of claim 9, further comprising a temperature sensor located in or adjacent to the anode.

14. The microbial monitoring system of claim 9, wherein the device is further configured to measure a current between the anode and the cathode.

15. The microbial monitoring system of claim 9, further comprising a connector for connecting the anode to the cathode assembly.

16. The microbial sensor system of claim 1, further comprising a temperature probe embedded within the anode.

17. The microbial sensor system of claim 1, further comprising an anode body connected to at least one of the one or more anodes.

18. The microbial sensor system of claim 17, further comprising an anode connector connected to the anode body.

19. The microbial sensor system of claim 1, further comprising a cathode body coupled to the cathode.

20. The microbial sensor system of claim 1, further comprising a gas-permeable membrane coupled to the cathode body.

* * * * *